(12) United States Patent
Li et al.

(10) Patent No.: US 8,939,011 B2
(45) Date of Patent: Jan. 27, 2015

(54) ON-LINE ANALYZER FOR VOCS AND METHOD OF USING THE SAME

(75) Inventors: Hongjie Li, Wuhan (CN); Changmian Han, Wuhan (CN); Maogui Jiang, Wuhan (CN); Pengjiao Wang, Wuhan (CN)

(73) Assignee: Wuhan Tianhong Instruments Co., Ltd (CN)

( * ) Notice: Subject to any disclaimer, the term of this patent is extended or adjusted under 35 U.S.C. 154(b) by 0 days.

(21) Appl. No.: 14/344,674

(22) PCT Filed: Jul. 20, 2012

(86) PCT No.: PCT/CN2012/000980
§ 371 (c)(1),
(2), (4) Date: Mar. 13, 2014

(87) PCT Pub. No.: WO2013/037182
PCT Pub. Date: Mar. 21, 2013

(65) Prior Publication Data
US 2014/0318217 A1    Oct. 30, 2014

(30) Foreign Application Priority Data
Sep. 16, 2011    (CN) .......................... 2011 1 0274853

(51) Int. Cl.
| | |
|---|---|
| *G01N 1/00* | (2006.01) |
| *G01N 30/06* | (2006.01) |
| *G01N 30/78* | (2006.01) |
| *G01N 30/02* | (2006.01) |
| *G01N 30/88* | (2006.01) |

(52) U.S. Cl.
CPC ................ *G01N 30/06* (2013.01); *G01N 30/78* (2013.01); *G01N 2030/025* (2013.01); *G01N 2030/8854* (2013.01)
USPC ....................................................... 73/23.41

(58) Field of Classification Search
CPC ................ G01N 2030/025; G01N 2030/8854; G01N 1/405; G01N 30/02; G01N 30/06; G01N 30/12
USPC ....................................................... 73/23.41
See application file for complete search history.

(56) References Cited

U.S. PATENT DOCUMENTS
| | | | |
|---|---|---|---|
| 4,759,210 A | 7/1988 | Wohltjen | |
| 5,168,746 A | 12/1992 | Madhusudhan et al. | |
| 5,310,681 A | 5/1994 | Rounbehler et al. | |
| 5,321,984 A | 6/1994 | Stroupe | |
| 5,435,169 A | 7/1995 | Mitra | |

FOREIGN PATENT DOCUMENTS
| | | |
|---|---|---|
| CN | 2476819 Y | 2/2002 |
| CN | 1632570 A | 6/2005 |
| CN | 101609072 A | 12/2009 |
| CN | 102375041 A | 3/2012 |
| CN | 202256359 U | 5/2012 |
| WO | 9422009 A2 | 9/1994 |

OTHER PUBLICATIONS

Deng, Qifa et al., Method and study of determining air volatile organic compounds by GC/MS, Northern Environment, Feb. 2011, vol. 23, No. I-2, pp. 134-135,140.
Fang, Shuangxi et al., Dual channel GC system for measuring background atmospheric CH4, CO, N2O and SF6, Acta Scientiae Circumstantiae, Jan. 2010, vol. 30, No. 1, pp. 52-59.
International Search Report for Application No. PCT/CN2012/000980 dated Nov. 8, 2012.
Xie, Lanying et al., Thermoelectric condensation of VOCs , Guangdong Chemical Industry, 2005, No. 6, pp. 11-14.

*Primary Examiner* — Hezron E Williams
*Assistant Examiner* — Rodney T Frank
(74) *Attorney, Agent, or Firm* — Lerner, David, Littenberg, Krumholz & Mentlik, LLP

(57) ABSTRACT

The present invention relates to an on-line analyzer for VOCs in gas and method of using the same, comprising: a sampling device, a gas supply device and a refrigerating device connected to the sampling device and the gas supply device respectively; the on-line analyzer for VOCs in gas with two cryo-focuses in empty tubes and two detectors also comprises a gas flow control device connected to the sampling device and the gas-supply device respectively, an analyzing device connected to the gas flow control device, and a data acquisition and processing device connected to the analyzing device. Therefore, the present invention has a following advantage: the present invention runs automatically and continuously over a long period since it uses electronic refrigeration technique to achieve cryo-refrigeration, instead of using liquid nitrogen refrigeration technique which needs frequent addition of liquid nitrogen and limits application conditions.

6 Claims, 1 Drawing Sheet

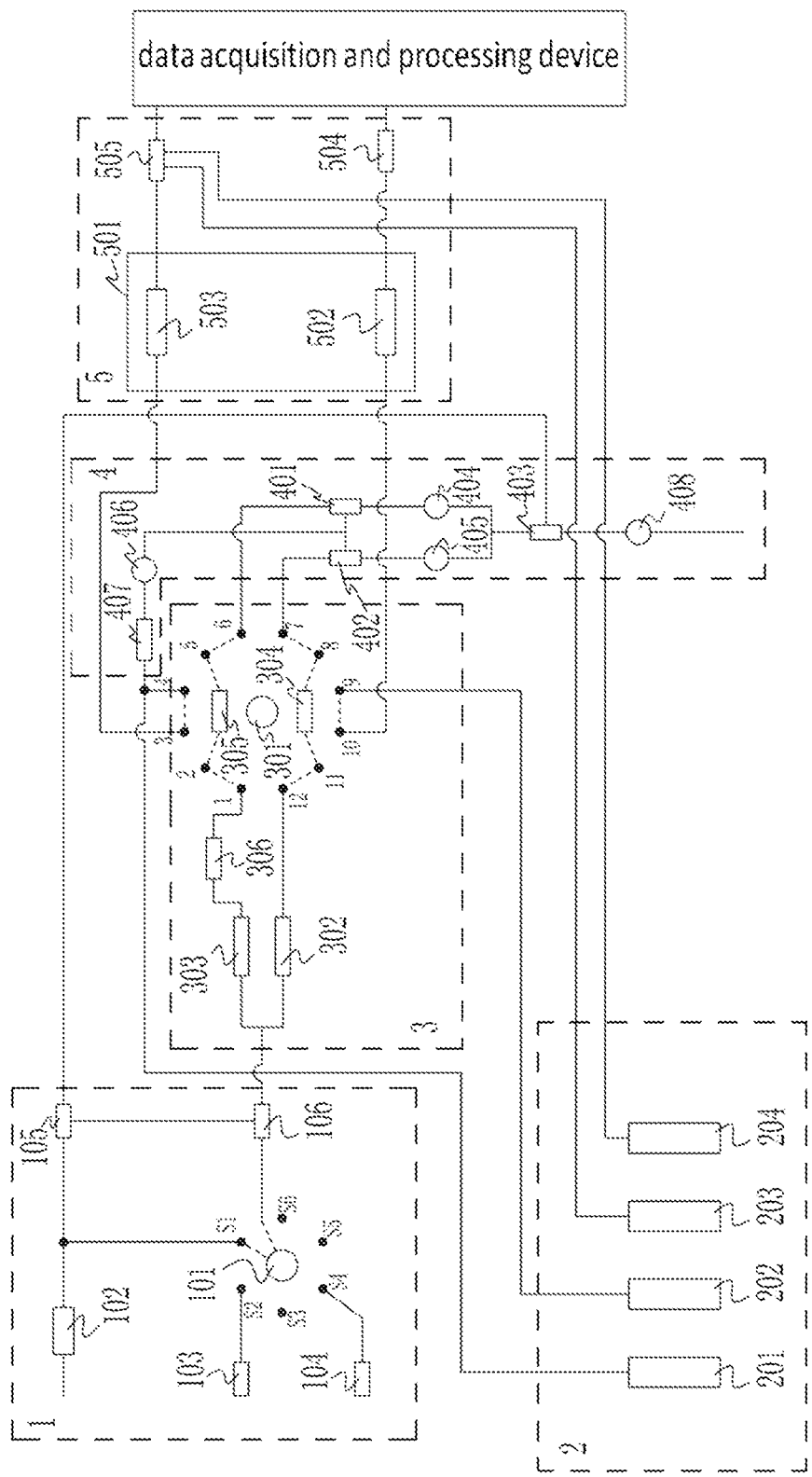

ON-LINE ANALYZER FOR VOCS AND METHOD OF USING THE SAME

The present application is a national phase entry under 35 U.S.C. §371 of International Application No. PCT/CN2012/000980 filed Jul. 20, 2012, published in Chinese, which claims priority from Chinese Patent Application No. 201110274853.0 filed Sep. 16, 2011, all of which are hereby incorporated herein by reference.

BACKGROUND

The present invention generally relates to an analyzer for VOCs (Volatile Organic Compounds) in gas and a method of using the same. More particularly, the present invention relates to an on-line analyzer for VOCs in gas and method of using the same.

Volatile Organic Compounds (VOCs) refer to organic chemical compounds that have boiling points roughly in the range of 50° C.-260° C. and saturation vapor pressures above 133.322 Pa on room-temperature conditions. These compounds commonly exist in indoor and outdoor air, and play an import role in increasing tropospheric ozone and generating other oxidants, and may directly produce secondary pollutants, such as organic aerosols. More significantly, some compounds in components of VOCs, such as benzene, 1,3-butadiene etc, have potentially carcinogenic effect. Therefore, it is brought to the attention of the people and becomes an important point of domestic and foreign research, to study the existence, source, distribution regularity and transformation of VOCs in environment and their effect on human health. It is a necessary means for conducting this research to establish a simple and reliable method of sampling and measuring VOCs that have complicated components and extremely small content.

Nowadays, the widely-used methods of analyzing VOCs in air include 1) field sampling-laboratory analysis system and 2) field on-line continuous automatic monitoring system.

The field sampling method of field sampling-lab analyzing system mainly includes bag sampling, stainless steel canister sampling and adsorbent tube sampling. Bag sampling is rarely used now because its inner surface absorbs VOC; stainless steel canister sampling has a well sampling effect, but in this method, it is complex and costly to apply liquid nitrogen to freezingly preconcentrate the sample gas, which needs frequent addition of liquid nitrogen; absorbent tube sampling has some problems, such as low efficiency of absorption and desorption of VOCs, high disturbance of adsorbents and replacement of absorbent tubes and the like. Laboratory analysis methods mainly include gas chromatographic method (GC) (gas chromatographic/hydrogen flame ionization detector/photo-ionization detector) (GC/FID/PID), gas chromatographic/mass-spectrography (GC/MS). In field sampling-laboratory analysis system. The main disadvantage of this system in analyzing VOCs in gas is that it cannot realize real-time continuous automatic monitoring of VOCs in ambient atmospheres and cannot capture the rapid change of concentration of VOCs in air.

At present, analysis principle of the field on-line continuous automatic monitoring system monitoring system mainly involves absorbent tube sampling (room-temperature/low-temperature)/thermal desorption gas chromatography, and the detectors therefor are hydrogen flame ionization detector (FID) and photoionization detector (PID). The main disadvantages of the on-line analyzing system involve problems existing in absorbent tube sampling, such as absorption/desorption efficiencies of different VOCs and replacement of absorbent tubes, both of the two detectors of FID and PID having no specificity for the qualitative analysis of VOCs and having selectivity for the detecting of different VOCs (FID is only used to detect hydrocarbons. PID cannot detect a portion of hydrocarbons C2 and C3, such as ethane and propane, a portion of halogenated hydrocarbons, such as dichloromethane, chloroform, ethylene dichloride and the like, and compounds containing oxygen (nitrogen, sulphur), such as methanol, acrylonitrile, carbonyl sulfide and the like). Therefore, currently, the on-line analyzer for VOCs is mainly used to analyze hydrocarbons C2-C12, and hydrocarbons C2-C5 and hydrocarbons C6-C12 are detected by two analyzers respectively, instead of simultaneously analyzing and detecting hydrocarbons C2-C12, VOCs containing oxygen (nitrogen, sulphur) and halogenated hydrocarbons.

At present, the research on VOCs in ambient atmospheres starts late and the sampling and analyzing of VOCs in air relay on foreign large analytical equipments and instruments, which are costly, complicated in analyzing process and unable to perform real-time on-line continuous automatic analysis, which has a large gap from the actual needs of research of air pollution. Therefore, it is important in a field of atmospheric environment monitoring and research, to seek a new sampling method and analyzing technique of VOCs, develop a analyzer of VOCs with high sensitivity, simple operation, cost-efficient and easy maintenance, and develop a on-line continuous automatic monitoring technique of VOCs.

SUMMARY

One aspect of the present invention is directed to solve the problems in existing technology, such as frequent addition of liquid nitrogen required by liquid nitrogen refrigeration technique, limitation of application conditions and automation. The embodiments of the present invention provide an on-line analyzer for VOCs and a method of using the same, that apply electronic cryogenic refrigeration technique and method to simplify the operation procedures of analyzing system, achieve long-term and continuous operation, and facilitate automation, and method of thereof.

Yet another aspect of the present invention is directed to solve the problems in existing technology that applies absorbent tubes for sampling, such as low absorption efficiency of a portion of VOCs, replacement of absorbent tubes and the like. The embodiments of the present invention provide an long life on-line analyzer for VOCs and a method of using the same, that apply empty capillary column to cryogenic condensation.

Still another aspect of the present invention is directed to solve the problems in existing on-line monitoring technology that uses a single gas path to sample and uses two instruments to detect hydrocarbons C2-C12. The embodiments of the present invention provide an on-line analyzer for VOCs and a method of using the same, that use two gas paths to sample simultaneously and concentrate hydrocarbons C2-C5 and C5-C12 respectively, and a single instrument to simultaneously detect hydrocarbons C2-C12.

Another aspect of the present invention is directed to solve the problems in existing on-line monitoring technology that uses selective detectors (FID and PID), such as less types of VOCs to be detected. The embodiments of the present invention provide an on-line analyzer for VOCs and a method of using the same, that utilize a detection technique and method using FID detector and MS detector to simultaneously analyze and detect VOCs such as hydrocarbons C2-C12, compounds containing O (N, S) and halogenated hydrocarbons.

Yet another aspect of the present invention is directed to solve the problems in existing on-line analysis for VOCs in air, such as the incompatibility of field sampling-laboratory analysis and field on-line continuous automatic monitoring. The embodiments of the present invention provide an on-line analyzer for VOCs and a method of using the same that can be used in both of field sampling (canister sampling)-laboratory analysis and field on-line continuous automatic monitoring VOCs.

Above problems of the prior art can be solved by the following solutions:

An on-line analyzer for VOCs in gas comprising a sampling device; a gas-supply device; and a refrigerating device connected to the sampling device and the gas-supply device respectively; wherein the on-line analyzer for VOCs uses two cryo-focuses in empty tubes and two detectors, also comprises a gas flow control device connected to the sampling device and the gas-supply device respectively, an analyzing device connected to the gas flow control device, and a data acquisition and processing device connected to the analyzing device.

In above on-line analyzer for VOCs in gas, the sampling device comprises: an 6-way valve; and a filter, an inlet tube for sample gas (continuous sample or single sample injection can be selected by setting the software), an inlet tube for internal standards, an inlet tube for external standards, a first solenoid valve and a second solenoid valve connected to the 6-way valve respectively, wherein the first solenoid valve is connected to the second solenoid valve.

In the above on-line analyzer for VOCs in gas, the refrigerating device comprises: a 12-way valve; and a first dewatering tube, a second dewatering tube, a first concentrating tube and a second concentrating tube connected to the 12-way valve respectively, wherein the first dewatering tube and the second dewatering tube are connected to the second solenoid valve simultaneously.

In the above on-line analyzer for VOCs in gas, the refrigerating device also comprises a trapping tube for CO2, the second dewatering tube is connected to the 12-way valve through the trapping tube for CO2, and the first dewatering tube, the second dewatering tube, the first concentrating tube and the second concentrating tube are disposed in a cryotrap.

In the above on-line analyzer for VOCs in gas, the gas flow control device comprises: a third solenoid valve; a forth solenoid valve; a first mass flow controller and a second mass flow controller connected to the third solenoid valve and the forth solenoid valve respectively; a third mass flow controller connected to the third solenoid valve and the forth solenoid valve simultaneously; a fifth solenoid valve connected to the first mass flow controller, the second mass flow controller, the first solenoid valve and a sampling pump simultaneously; and a pressure reducing valve connected to the third solenoid valve and the forth solenoid valve through the third mass flow controller simultaneously.

In the above on-line analyzer for VOCs in gas, the analyzing device comprises: an oven; a first capillary column and a second capillary column, disposed in the oven and connected to the 12-way valve respectively; a first detector connected to the first capillary column; and a second detector connected to the second capillary column.

In the above on-line analyzer for VOCs in gas, the gas-supply device comprises: a nitrogen-supply device; a helium-supply device; an air-supply device; and a hydrogen-supply device; wherein the nitrogen-supply device is connected to the pressure reducing valve, the helium-supply device is connected to the 12-way valve, both of the air-supply device and the hydrogen-supply device are connected to the second detector; the first detector is MS (mass spectrum) detector and the second detector is hydrogen FID detector.

In the above on-line analyzer for VOCs in gas, both of the first dewatering tube and the second dewatering tube are empty glass tube or empty silica tube with an inner diameter of 1.0-1.5 mm and a length of 30-40 cm; the outer walls of both of the first dewatering tube and the second dewatering tube are bound with temperature-adjustable and temperature-controllable heating wire; both of the first concentrating tube and the second concentrating tube are empty capillary column with an inner diameter of 0.53 mm and a length of 30-40 cm, the first concentrating tube is activated silica capillary column and the second concentrating tube is PLOT capillary column; the outer walls of both of the first concentrating tube and the second concentrating tube are bound by temperature-adjustable and temperature-controllable heating wire.

In the above on-line analyzer for VOCs in gas, the trapping tube for CO2 is polytetrafluoroethylene tube or glass tube having an inner diameter of 4 mm and a length of 15 cm, and the tube is filled with alkali asbestos.

A method of on-line analyzing VOCs by using the on-line analyzer for VOCs in gas with two cryo-focuses in empty tubes and two detectors, comprises the steps of:

Step1, gathering the sample gas, wherein when a sampling pump is turned on, the sample gas flows into a sampling gas path through a filter, enters an inlet (S1) of a 6-way valve and exits from a common outlet (S6); the sample gas is divided into two branches after going through the second solenoid valve:

the sample gas in the first gas path passes through a first dewatering tube to enter port 12 of 12-way valve, and then enters a first concentrating tube through port 11; the VOCs of hydrocarbon C4-C12, organic compounds containing O (N, S) and halogenated hydrocarbons are coldly concentrated in the first concentrating tube; other gases enter port 8 of the 12-way valve and exit from port 7, flow through a forth solenoid valve to a fifth solenoid valve though a second mass flow controller, and are discharged by the sampling pump;

the sample gas in the second gas path enters a second dewatering tube, enters port 1 of the 12-way valve through a trapping tube for CO2, and then enters a second concentrating tube through port 2; hydrocarbons C2-C5 are coldly concentrated in the second concentrating tube quantificationally; other gases enter port 5 of the 12-way valve and exit from port 6, flow through a third solenoid valve, a first mass flow controller and the fifth solenoid valve, and are discharged by the sampling pump;

in this step, the temperature of the first dewatering tube is −20° C. and the temperature of the second dewatering tube is −80° C. Both of the temperatures of the first concentrating tube and the second concentrating tube are −155° C.;

Step2, conducting thermal desorption, qualitative and quantitative analysis of the sample gas gathered in step 1, wherein the first concentrating tube and the second concentrating tube are quickly heated with a speed of 40° C./s simultaneously, and after they are heated from −155° C. to 100° C., VOCs in the two concentrating tubes are subjected to quick desorption; detailed operations are as follows:

in the first gas path, helium gas from a helium-supply device flows from port 9 of the 12-way valve, exits from port 8 of the 12-way valve, then enters into the first concentrating tube; with helium gas purging, the desorbed hydrocarbons C5-C12, compounds containing O (N, S) and halogenated hydrocarbons and the like enter an oven through ports 11 and 10 of the 12-way valve, are separated in a first capillary column, and then enter a first detector for qualitative and quantitative analysis; the first capillary column has a inner diameter of 0.25 mm and a length of 60 m;

in the second gas path, nitrogen gas from a nitrogen-supply device enter the second concentrating tube through ports 4 and 5 of the 12-way valve; with nitrogen gas purging, the desorbed hydrocarbons C2-C5 enter the oven through ports 2 and 3 of 12-way valve, are separated in a second capillary column and then enter a second detector for qualitative and quantitative analysis; the second capillary column has a inner diameter of 0.32 mm and a length of 15 m; during thermal desorption of the first concentrating tube and the second concentrating tube, the refrigeration continues and the temperature of cryotrap remains about −155° C.;

during the analysis, the data are collected by a data acquisition systems; and after the completion of analysis, the collected data are processed by a data processing device.

Step 3, conducting heating and back purging purification, wherein the first dewatering tube, the second dewatering tube, the first concentrating tube and the second concentrating tube are heated to a temperature of 100° C. or higher, and the temperature of cryotrap remains about −155° C. The purging gas of nitrogen gas from the nitrogen-supply device is divided into two branches through a pressure reducing valve and a third mass flow controller:

nitrogen gas flows through the forth solenoid valve, ports 7 and 8 of the 12-way valve to backpurge the first concentrating tube, enters the first dewatering tube through ports 11 and 12 of the 12-way valve to purge the water in tubes, flows through the second solenoid valve and the first solenoid valve, and finally flows through the fifth solenoid valve to be discharged by the sampling pump;

nitrogen gas flows through the third solenoid valve, ports 6 and 5 of 12-way valve to backpurge the second concentrating tube, enters the trapping tube for CO2 through ports 2 and 1 of the 12-way valve, enters the second dewatering tube, flows through second solenoid valve and the first solenoid valve, and finally flows through the fifth solenoid valve to be discharged by the sampling pump.

Therefore, the present invention has the following advantages: 1. The present invention runs automatically and continuously over a long period since it uses electronic refrigeration technique to achieve cryo-refrigeration, instead of using liquid nitrogen refrigeration technique which needs frequent addition of liquid nitrogen and limits application conditions; 2. The present invention has high concentration/adsorption efficiency, runs automatically and continuously over a long period, since it applies empty capillary column for cold concentration of VOCs, avoiding the low absorption/desorption efficiency of a portion of organic compounds in the absorption and concentration and replacement of absorbent tubes, achieving a long-term, continuous and convenient operation and automation; 3. The present invention can concentrate hydrocarbons C2-C5 and hydrocarbons C5-C12, compounds containing O (N, S) and halogenated hydrocarbons respectively since it use cold concentration technique with two empty capillary columns; 4. The present invention can simultaneously analyze hydrocarbons C2-C12, compounds containing O (N, S) and halogenated hydrocarbons and the like since it uses the analytical technique with two analytical columns and two detectors and combines the selective detector (FID) with universal detector (MS), improves the ability of qualitative and quantitative analysis of VOCs; 5. The present invention provides two functions of sampling: continuous sampling and single sampling, that is, the present invention can perform singe sampling operation in the laboratory to analyze the sample gathered in the field sampling canisters, and can be installed in automatic monitoring station to perform on-line continuous automatic monitoring.

BRIEF DESCRIPTION OF THE DRAWINGS

The present invention will become more fully understood from the detailed description given hereinafter and the accompanying drawings which are given by way of illustration only, and thus are not limitative of the present invention and wherein:

FIG. 1 illustrates the principle according to an embodiment of the present invention, wherein

1(101-106) represents the sampling device.
2(201-204) represents the gas-supply device.
3(301-306) represents the refrigerating device.
4(401-408) represents the gas controlling device.
5(501-505) represents the analyzing and detecting device.

DETAILED DESCRIPTION

For a fuller understanding of the nature and advantages of the present invention, reference should be made to the ensuing detailed description and the accompanying drawings. Other aspects, objects and advantages of the invention will be apparent from the drawings and the detailed description that follows.

Embodiments

An on-line analyzer for VOCs in gas comprises a sampling device 1; a gas-supply device 2; and a refrigerating device 3 connected to the sampling device 1 and the gas-supply device 2 respectively; wherein the on-line analyzer for VOCs uses two cryo-focuses in empty tubes and two detectors, also comprises a gas flow control device 4 connected to the sampling device 1 and the gas-supply device 2 respectively, an analyzing device 5 connected to the gas flow control device 4, and a data acquisition and processing device connected to the analyzing device 5.

The sampling device 1 comprises: a 6-way valve 101; and a filter 102, an inlet tube for internal standards 103, an inlet tube for external standards 104, a first solenoid valve 105 and a second solenoid valve 106 connected to the 6-way valve 101 respectively, wherein the first solenoid valve 105 is connected to the second solenoid valve 106.

The refrigerating device 3 comprises: a 12-way valve 301; and a first dewatering tube 302, a second dewatering tube 303, a first concentrating tube 304 and a second concentrating tube 305 connected to the 12-way valve 301 respectively, wherein the first dewatering tube 302 and the second dewatering tube 303 are connected to the second solenoid valve 106 simultaneously. Both of the first dewatering tube 302 and the second dewatering tube 303 are empty glass tube or empty silica tube having an inner diameter of 1.0-1.5 mm and a length of 30-40 cm; the outer walls of both of the first dewatering tube 302 and the second dewatering tube 303 are bound with temperature-adjustable and temperature-controllable heating wire; both of the first concentrating tube 304 and the second concentrating tube 305 are empty capillary column having an inner diameter of 0.53 mm and a length of 30-40 cm, the first concentrating tube 304 uses a deactivated silica capillary column and the second concentrating tube 305 uses PLOT capillary column; the outer walls of both of the first concentrating tube 304 and the second concentrating tube 305 are bound with temperature-adjustable and temperature-controllable heating wire.

The refrigerating device 3 also comprises a trapping tube for CO2 306, the second dewatering tube 303 is connected to the 12-way valve 301 through the trapping tube for CO2 306.

The first dewatering tube 302, the second dewatering tube 303, the first concentrating tube 304 and the second concentrating tube 305 are disposed in a cryotrap. The trapping tube for CO2 306 is polytetrafluoroethylene tube or glass tube having an inner diameter of 4 mm and a length of 15 cm, and the tube is filled with alkali asbestos, with each end filled with glass wool of 1 cm to fix and prevent the alkali asbestos being blew away by gas.

The gas flow control device 4 comprises: a third solenoid valve 401; a forth solenoid valve 402; a first mass flow controller 404 and a second mass flow controller 405 connected to the third solenoid valve 401 and the forth solenoid valve 402 respectively; a third mass flow controller 406 connected to the third solenoid valve 401 and the forth solenoid valve 402 simultaneously; a fifth solenoid valve 403 connected to the first mass flow controller 404, the second mass flow controller 405, the first solenoid valve 105 and a sampling pump 408 simultaneously; and a pressure reducing valve 407 connected to the third solenoid valve 401 and the forth solenoid valve 402 through the third mass flow controller 406 simultaneously.

The analyzing device 5 comprises: an oven 501; a first capillary column 502 and a second capillary column 503 disposed in the oven 501 and connected to the 12-way valve 301 respectively; a first detector 504 connected to the first capillary column 502; and a second detector 505 connected to the second capillary column 503. The oven has the functions of heating, programmed temperature raising and controlling, and can be equipped with two capillary columns of 60 m and two injectors, and connected with two detectors. The injectors and detectors have the functions of heating and temperature controlling.

The gas-supply device 2 comprises: a nitrogen-supply device 201; a helium-supply device 202; an air-supply device 203; and a hydrogen-supply device 204. The nitrogen-supply device 201 is connected to the pressure reducing valve 407, the helium-supply device 202 is connected to the 12-way valve 301, and both of the air-supply device 203 and the hydrogen-supply device 204 are connected to the second detector 505. The first detector 504 may be a MS detector and the second detector 505 may be a hydrogen FID detector.

The present invention provides a method of analyzing VOCs by using the on-line analyzer for VOCs in air, comprising the steps of:

Step 1, gathering the sample gas, wherein when a sampling pump 408 is turned on, the sample gas flows into a sampling gas path through a filter 102, enters an inlet 51 of a 6-way valve 101 and exits from a common outlet S6; the sample gas is divided into two branches after going through the second solenoid valve 106;

the sample gas in the first gas path passes through a first dewatering tube 302 to enter port 12 of 12-way valve 301, and then enters a first concentrating tube 304 through port 11; the VOCs of hydrocarbon C4-C12, organic compounds containing O (N, S) and halogenated hydrocarbons are coldly concentrated in the first concentrating tube 304; other gases enter port 8 of the 12-way valve 301 and exit from port 7, flow through a forth solenoid valve 402, flow though a second mass flow controller 405, and flow through a fifth solenoid valve 403, and are discharged by the sampling pump 408;

the sample gas in the second gas path enters a second dewatering tube 303, enters port 1 of the 12-way valve 301 through a trapping tube for CO2 306, and then enters a second concentrating tube 305 from port 2; hydrocarbons C2-C5 are coldly concentrated in the second concentrating tube 305 quantificationally; other gases enter port 5 of the 12-way valve 301 and exit from port 6, flow through a third solenoid valve 401, a first mass flow controller 404 and the fifth solenoid valve 403, and are discharged by the sampling pump 408;

after completing the sampling procedure of sample gas, a data acquisition and processing device analyzes the data in the analyzing device;

in this step, the temperature of the first dewatering tube 302 is −20° C. and the temperature of the second dewatering tube 303 is −80° C. Both of the temperatures of the first concentrating tube 304 and the second concentrating tube 305 are about −155° C.

Step 2, conducting thermal desorption of the sample gas gathered in step 1, wherein the first concentrating tube 304 and the second concentrating tube 305 are quickly heated simultaneously, and after they are heated from −155° C. to 100° C. with a speed of 40° C./s, VOCs in the two concentrating tubes are subjected to quick desorption; detailed operations are as follows:

in the first gas path, helium gas from a helium-supply device 202 flows from port 9 of the 12-way valve 301, exits from port 8 of the 12-way valve 301, then enters into the first concentrating tube 304; with helium gas purging, the desorbed hydrocarbons C5-C12, compounds containing O (N, S) and halogenated hydrocarbons and the like enter an oven 501 through ports 11 and 10 of the 12-way valve 301, are separated in a first capillary column 502, and then enter a first detector 504 for qualitative and quantitative analysis; the first capillary column is a capillary column with a inner diameter of 0.25 mm and a length of 60 m;

in the second gas path, nitrogen gas from a nitrogen-supply device 201 enter the second concentrating tube 305 through ports 4 and 5 of the 12-way valve 301; with nitrogen gas purging, the desorbed hydrocarbons C2-C5 enter the oven 501 through ports 2 and 3 of 12-way valve 301, are separated in a second capillary column 503 and then enter a second detector 505 for qualitative and quantitative analysis of the desorbed hydrocarbons C2-C5; the second capillary column is a capillary column with a inner diameter of 0.32 mm and a length of 15 m; during thermal desorption of the first concentrating tube 304 and the second concentrating tube 305, the refrigeration continues and the temperature of cryotrap remains −155° C. to −150° C.

Upon start of the thermal desorption, a data acquisition and processing device begins to gather, process and analyze the data synchronously.

Step 3, conducting heating and back purging purification, wherein the first dewatering tube 302, the second dewatering tube 303, the first concentrating tube 304 and the second concentrating tube 305 are heated to a temperature of 100° C. or higher, and the temperature of cryotrap remains −155° C. to −150° C. The purging gas of nitrogen gas from the nitrogen-supply device 201 is divided into two branches through a pressure reducing valve 407 and a third mass flow controller 406;

nitrogen gas flows through the forth solenoid valve 402, ports 7 and 8 of the 12-way valve 301 to backpurge the first concentrating tube 304, enters the first dewatering tube 302 through ports 11 and 12 of the 12-way valve 301 to purge the water in tubes, flows through the second solenoid valve 106 and the first solenoid valve 105, and finally flows through the fifth solenoid valve 403 to be discharged by the sampling pump 408;

nitrogen gas flows through the third solenoid valve 401, ports 6 and 5 of 12-way valve 301 to backpurge the second concentrating tube 305, enters the trapping tube for CO2 306 through ports 2 and 1 of the 12-way valve 301, enters the second dewatering tube 303, flows through second solenoid valve 106 and the first solenoid valve 105, and finally flows through the fifth solenoid valve 403 to be discharged by the sampling pump 408.

The present invention is used to automatically and continuously monitor volatile hydrocarbons C2-C12, organic compound containing O (N, S) and halogenated hydrocarbons in air. In these embodiments, the cryotrap is described in Chinese Patent No. 200810118237.4.

It is understood that the examples and embodiments described herein are for illustrative purposes and that various modifications or changes in light thereof will be suggested to a person skilled in the art and are to be included within the spirit and purview of this application and the scope of the appended claims.

Although specific terms are employed herein, such as, sampling device 1, 6-way valve 101, filter 102, inlet tube for internal standards 103, inlet tube for external standards 104, first solenoid valve 105, second solenoid valve 106, gas-supply device 2, nitrogen-supply device 201, helium-supply device 202, air-supply device 203, hydrogen-supply device 204, refrigerating device 3, 12-way valve 301, first dewatering tube 302, second dewatering tube 303, first concentrating tube 304, second concentrating tube 305, trapping tube for CO2 306, gas flow control device 4, third solenoid valve 401, forth solenoid valve 402, fifth solenoid valve 403, first mass flow controller 404, second mass flow controller 405, third mass flow controller 406, pressure reducing valve 407, sampling pump 408, analyzing device 5, oven 501, first capillary column 502, second capillary column 503, first detector 504, second detector 505 and the like, they are used in a generic and descriptive sense only and not for purposes of limitation. It will be apparent to those skilled in the art that various modifications and variations can be made without departing from the scope or spirit of the present invention.

What is claimed is:

1. An on-line analyzer for VOCs in gas comprising:
   a sampling device;
   a gas-supply device; and
   a refrigerating device connected to the sampling device and the gas supply device respectively,
   wherein the on-line analyzer for VOCs uses two cryo-focuses in empty tubes and two detectors, also comprises:
      a gas flow control device connected to the sampling device and the gas supply device respectively;
      an analyzing device connected to the gas flow control device; and
      a data acquisition and processing device connected to the analyzing device,
   wherein the sampling device comprises:
      a 6-way valve; and
      a filter, an inlet tube for internal standards, an inlet tube for external standards, a first solenoid valve and a second solenoid valve which are connected to the 6-way valve respectively,
      wherein the first solenoid valve is connected to the second solenoid valve,
   wherein the refrigerating device comprises:
      a 12-way valve; and
      a first dewatering tube, a second dewatering tube, a first concentrating tube and a second concentrating tube connected to the 12-way valve respectively,
      wherein the first dewatering tube and the second dewatering tube are connected to the second solenoid valve simultaneously,
   wherein the refrigerating device also comprises a trapping tube for $CO_2$,
   wherein the second dewatering tube is connected to the 12-way valve through the trapping tube for $CO_2$,
   wherein the first dewatering tube, the second dewatering tube, the first concentrating tube and the second concentrating tube are disposed in a cryotrap.

2. The on-line analyzer for VOCs in gas of claim 1, wherein the gas flow control device comprises:
   a third solenoid valve;
   a forth solenoid valve;
   a first mass flow controller and a second mass flow controller connected to the third solenoid valve and the forth solenoid valve respectively;
   a third mass flow controller connected to the third solenoid valve and the forth solenoid valve simultaneously;
   a fifth solenoid valve connected to the first mass flow controller, the second mass flow controller, the first solenoid valve and a sampling pump simultaneously; and
   a pressure reducing valve connected to the third solenoid valve and the forth solenoid valve through the third mass flow controller simultaneously.

3. The on-line analyzer for VOCs in gas of claim 2, wherein the analyzing device comprises:
   an oven;
   a first capillary column and a second capillary column, disposed in the oven and connected to the 12-way valve respectively;
   a first detector connected to the first capillary column; and
   a second detector connected to the second capillary column.

4. The on-line analyzer for VOCs in gas of claim 3, wherein the gas-supply device comprises:
   a nitrogen-supply device;
   a helium-supply device;
   an air-supply device; and
   a hydrogen-supply device,
   wherein the nitrogen-supply device is connected to the pressure reducing valve, the helium-supply device is connected to the 12-way valve, and both of the air-supply device and the hydrogen supply device are connected to the second detector,
   wherein the first detector is a MS detector and the second detector is a hydrogen FID detector.

5. The on-line analyzer for VOCs in gas of claim 1, wherein both of the first dewatering tube and the second dewatering tube are empty glass tube or empty silica tube with an inner diameter of 1.0-1.5 mm and a length of 30-40 cm;
   wherein the outer walls of both of the first dewatering tube and the second dewatering tube are bound with temperature-adjustable and temperature-controllable heating wire;
   wherein both of the first concentrating tube and the second concentrating tube are empty capillary column with an inner diameter of 0.53 mm and a length of 30-40 cm,
   wherein the first concentrating tube uses an activated silica capillary column and the second concentrating tube uses PLOT capillary column;
   wherein the outer walls of both of the first concentrating tube and the second concentrating tube are bound with temperature-adjustable and temperature-controllable heating wire.

6. The on-line analyzer for VOCs in gas of claim 1, wherein the trapping tube for $CO_2$ is a polytetrafluoroethylene tube with a inner diameter of 4 mm and a length of 15 cm, and the tube is filled with alkali asbestos.

* * * * *